(12) United States Patent
Takemoto et al.

(10) Patent No.: US 8,703,789 B2
(45) Date of Patent: Apr. 22, 2014

(54) COMPOSITIONS INCORPORATING SESAMIN-CLASS COMPOUNDS AND VITAMIN B1 CLASS COMPOUNDS

(75) Inventors: Daisuke Takemoto, Osaka (JP); Yoshiko Ono, Osaka (JP); Yoko Yasutake, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 483 days.

(21) Appl. No.: 12/678,583

(22) PCT Filed: Sep. 17, 2008

(86) PCT No.: PCT/JP2008/066772
§ 371 (c)(1),
(2), (4) Date: Mar. 17, 2010

(87) PCT Pub. No.: WO2009/038095
PCT Pub. Date: Mar. 26, 2009

(65) Prior Publication Data
US 2010/0184793 A1 Jul. 22, 2010

(30) Foreign Application Priority Data
Sep. 19, 2007 (JP) .................................. 2007-242965

(51) Int. Cl.
*A01N 43/78* (2006.01)

(52) U.S. Cl.
USPC ......................................................... 514/276

(58) Field of Classification Search
CPC .... C07D 415/00; C12P 17/167; A61K 31/36; A61K 51/0425
USPC .......................................... 514/276; 424/74
See application file for complete search history.

(56) References Cited

U.S. PATENT DOCUMENTS

| | | |
|---|---|---|
| 5,180,588 A | 1/1993 | Shinmen et al. |
| 5,993,795 A * | 11/1999 | Osawa et al. .................... 424/74 |
| 2006/0115556 A1 * | 6/2006 | Foulger et al. .................. 426/72 |
| 2009/0054443 A1 | 2/2009 | Takemoto et al. |
| 2009/0092733 A1 | 4/2009 | Nakai et al. |

FOREIGN PATENT DOCUMENTS

| | | |
|---|---|---|
| CN | 1 836 555 A | 9/2006 |
| EP | 2 135 606 A1 | 12/2009 |
| JP | 4-9331 | 1/1992 |
| JP | 04-278067 | 10/1992 |
| JP | 4-278067 | 10/1992 |
| JP | H05-051388 | 2/1993 |
| JP | 2000-004832 | 1/2000 |
| JP | 2000-4832 | 1/2000 |
| JP | 2001-139579 | 5/2001 |
| JP | 2008-136391 | 6/2008 |
| WO | 2007/105757 | 9/2007 |
| WO | WO 2007/119378 A1 | 10/2007 |
| WO | WO 2008/126587 A1 | 10/2008 |

OTHER PUBLICATIONS

Moriura et al, Biol. Pharm. Bull., 19996, 19(1), 62-66.*
Naomi et al JP2005-023008 (Machine Translation).*
Kengo et al, JP05-051388 (Machine Translation).*
Ide et al, Biochim. Biophys. Acta, 2004, 1682, 80-91.*
Kinichiro et al JP2000-004832A (Machine Translation).*
El-Arab et al, J. Food Compos. Anal., 2004, 17, 81-97.*
International Search Report mailed Dec. 16, 2008 in International Application No. PCT/JP2008/066772 filed Sep. 17, 2008.
"Tila Taila Prayoga", In: Sodhala: 1978, P.V. Sharma, Oriental Institute, Baroda, XP002598278, 1 page.
Extended European Search Report in European Application No. 08832483.5 mailed Sep. 13, 2010.

* cited by examiner

*Primary Examiner* — Jason Sims
*Assistant Examiner* — Ibrahim D Bori
(74) *Attorney, Agent, or Firm* — Drinker Biddle & Reath LLP

(57) ABSTRACT

A composition incorporating at least one sesamin-class compound is enhanced in the anti-fatigue action of sesamin class compounds by additionally incorporating at least one vitamin $B_1$ class compound. Also provided is an anti-fatigue agent containing at least one sesamin-class compound and at least one vitamin $B_1$ class compound as the active ingredients.

8 Claims, 2 Drawing Sheets

COMPOSITIONS INCORPORATING SESAMIN-CLASS COMPOUNDS AND VITAMIN B1 CLASS COMPOUNDS

CROSS REFERENCE TO RELATED APPLICATIONS

This application is the National Stage of International Application No. PCT/JP2008/066772, filed Sep. 17, 2008, and claims benefit of Japanese Application No. 2007-242965, filed Sep. 19, 2007, both of which are herein incorporated by reference in their entirety.

TECHNICAL FIELD

The present invention relates to compositions that incorporate sesamin-class compounds and vitamin $B_1$ class compounds in order to enhance the physiological activating effects of sesamin-class compounds, more particularly their anti-fatigue action. The present invention also relates to anti-fatigue agents containing sesamin-class compounds and vitamin $B_1$ class compounds as the active ingredients.

BACKGROUND ART

Fatigue is a quantitative or qualitative decrease in the capacity for work and the efficiency of accomplishment that result from a bodily or mental activity, also accompanied by perceived feelings of fatigue including those of lassitude, discomfort and weakness. The reduced functions and the feelings of fatigue may occasionally occur simultaneously but they also occur with time lags or even independently. Such physiological fatigue is usually relieved by rest to restore the initial normal state and it will not last for long. According to "A Survey on Public Perception of Health" conducted by the Prime Minister's Office in 1985, over 60% of the people surveyed complained of fatigue but 70% of those who complained of fatigue said that "their fatigue is relieved by a night's sleep." However, this pattern is changing in recent years. According to the epidemiological research conducted by the fatigue survey study group of the Health and Welfare Ministry in 1999, the proportion of the people who perceived fatigue remained unchanged and accounted for about 60% but then as much as 60% of those people were reported to have felt tired for more than six months. Thus, in the 14 years from 1985 to 1999, more people became afflicted with chronic fatigue, indicating a change in the nature of fatigue (Nonpatent Literature 1). More recently, a disorder called "chronic fatigue syndrome (CFS)" and death by overwork are presenting themselves as big social problems. However, the causes of fatigue and its mechanism are of great variety and in spite of the work being conducted by many researchers, the entire picture of fatigue is yet to be seen and there have been established no definitive methods of treating or preventing fatigue-caused diseases including chronic fatigue syndrome and death by overwork.

Most recently, so-called "anti-fatigue substances" that have a fatigue-relieving action or an action for promoting the restoration of the normal state from fatigue have been reported. For example, certain kinds of amino acid compositions (Patent Literature 1), L-carnitine and histidine-related dipeptides (Patent Literature 2), hawthorn extracts (Patent Literature 3) and the like have been reported to have a body strength increasing action. In addition, nutrition support compositions containing ascorbic acid have been shown to be useful for the purpose of furnishing nutrition when one has lost their body strength due, for example, to exercise or at such times that one is tired (Patent Literature 4).

As regards sesamin-class compounds (hereinafter used as the collective term for sesamin and its analogs; sesamin analogs may be exemplified by espisesamin, as well as sesamin, sesaminol, episesaminol, sesamolin, and the like), experiments with purified sesamin-class compounds have led to the reporting of various actions including the action of inhibiting the metabolism of cholesterol and bile acid in the intestines (Patent Literature 5), the action of alleviating the symptoms of withdrawal from alcohol or tobacco intoxication (Patent Literature 6), the action of improving hepatic functions (Patent Literature 7), the action of in vivo stabilization of highly unsaturated fatty acids (Patent Literature 8), the action of inhibiting Δ5-desaturase (Patent Literature 9), the action of suppressing migraine (Patent Literature 10), the action of inducing apoptosis in human leukemic cells (Patent Literature 11), the action of suppressing the oxidative decomposition of melatonin (Patent Literature 12), and an autonomic nerve regulating action (Patent Literature 13).

Patent Literature 1: JP H09-124473 A
Patent Literature 2: JP 2001-046021 A
Patent Literature 3: JP H08-47381 A
Patent Literature 4: JP H06-327435 A
Patent Literature 5: JP Patent No. 3183664
Patent Literature 6: U.S. Pat. No. 4,427,694
Patent Literature 7: JP Patent No. 3075358
Patent Literature 8: JP H11-269456 A
Patent Literature 9: JP Patent No. 3070611
Patent Literature 10: JP 2003-183172 A
Patent Literature 11: JP 2001-151676 A
Patent Literature 12: JP 2000-143546 A
Patent Literature 13: WO 2004-105749
Nonpatent Literature 1: *Hiroh no kagaku* (Science of Fatigue) (9. *Hiroh kaifuku jyohoh* (Information on Recovery from Fatigue); 2001, Kodansha

DISCLOSURE OF THE INVENTION

Problems to be Solved by the Invention

As described above, various physiologically activating effects have been reported for sesamin-class compounds but there are very few reports on substances that can be used in combination with sesamin-class compounds to enhance their physiological activating effects.

An object, therefore, of the present invention is to provide sesamin-class compound incorporating compositions with enhanced physiological activating effects. Another object of the present invention is to provide agents having high physiological activating effects that contain sesamin-class compounds as the active ingredient.

Means of the Problems

The present inventors conducted intensive studies on the physiological activating effects of sesamin and already found that anti-fatigue actions (the action of relieving fatigue and the action of promoting recovery from fatigue) could be obtained by oral ingestion of sesamin. The present inventors continued their intensive studies and found that in compositions incorporating sesamin-class compounds (which refers to sesamin and its analogs; sesamin analogs are exemplified by episesamin, sesamin, sesaminol, episesaminol, sesamolin, and the like) and vitamin $B_1$ class compounds, the above-mentioned anti-fatigue actions of sesamin increased markedly beyond the range that was predictable from the actions of sesamin-class compounds alone and those of vitamin $B_1$ class compounds alone; the present invention has been accomplished on the basis of this finding.

Thus, the present invention relates to the following:
1. A composition incorporating at least one sesamin-class compound and at least one vitamin $B_1$ class compound, wherein the total amount of the sesamin-class compound incorporated is at least 1% of the total weight of the composition.
2. The composition as described in 1 above, wherein the sesamin-class compound is sesamin, episesamin, or a mixture thereof.
3. The composition as described in 1 or 2 above, wherein the vitamin $B_1$ class compound is at least one member selected from the group consisting of thiamin, thiamine disulfide, benfotiamin, fursultiamin, bisbentiamin, dicetiamin, thiamine ethyl disulfide, thiamine propyl disulfide, and salts thereof.
4. The composition as described in any one of 1 to 3 above, wherein the total amount of the vitamin $B_1$ class compound incorporated is between 0.001 and 20% of the total weight of the composition.
5. The composition as described in any one of 1 to 4 above, which is for oral use.
6. The composition as described in any one of 1 to 5 above, which is a food or a beverage.
7. A beverage containing at least one sesamin-class compound and at least one vitamin $B_1$ class compound, wherein the total content of the sesamin-class compound in 100 mL of the beverage is 1 to 100 mg and the total content of the vitamin $B_1$ class compound in 100 mL of the beverage is 1 to 100 mg.
8. An anti-fatigue agent containing at least one sesamin-class compound and at least one vitamin $B_1$ class compound as the active ingredients.
9. The anti-fatigue agent as described in 8 above, which is for treating or preventing chronic fatigue syndrome.
10. Use of a composition containing at least one sesamin-class compound and at least one vitamin $B_1$ class compound for producing an anti-fatigue agent.
11. A method of preventing or treating a fatigue condition, which comprises administering a composition containing at least one sesamin-class compound and at least one vitamin $B_1$ class compound to a subject in need.

Advantages of the Invention

Compositions incorporating sesamin-class compounds and vitamin $B_1$ class compounds are synergistically enhanced in their anti-fatigue actions (recovery from fatigue, relieving fatigue, and nutritional fortification) beyond the range that is predictable from the sesamin-class compounds and vitamin $B_1$ class compounds taken individually, with the result that the compositions have outstanding anti-fatigue actions.

The anti-fatigue agents of the present invention have remarkable actions for relieving fatigue and promoting recovery from fatigue and, what is more, they are safe not only in humans but also in non-human animals and can hence be administered continuously. Therefore, the anti-fatigue agents of the present invention are widely applicable as pharmaceutical compositions including physiologically functional foods.

Figure 1:
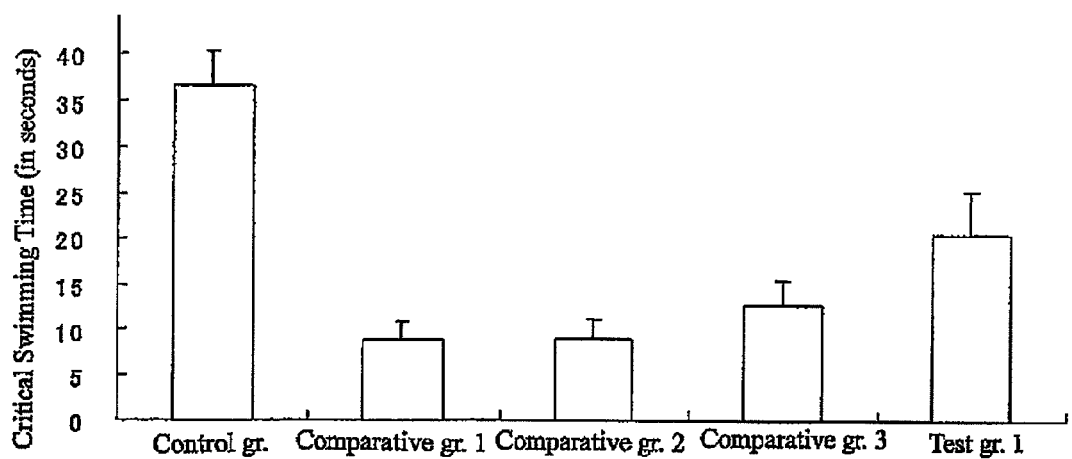
FIG. 1 shows critical swimming times for a normally kept group (control group), a group kept immersed in water (comparative group 1), a group of mice kept immersed in water under administration with 50 mg/kg of a vitamin $B_1$ class compound (comparative group 2), a group of mice kept immersed in water under administration with 50 mg/kg of sesamin-class compounds (comparative group 3), and a group of mice kept immersed in water under administration with 50 mg/kg of the vitamin $B_1$ class compound and 50 mg/kg of the sesamin-class compounds (test group 1)

BEST MODE FOR CARRYING OUT THE INVENTION (Sesamin-Class Compounds)

The sesamin-class compound of the present invention is the collective term for a series of compounds including sesamin and its analogs. Examples of the above-mentioned sesamin analogs include not only episesamin but also the dioxabicyclo[3.3.0]octane derivatives mentioned in JP H04-9331 A. Specific examples of the sesamin-class compound include sesamin, sesaminol, episesaminol, sesamolin, etc. and stereoisomers or racemic bodies of these compounds may be used either alone or in mixture. In the present invention, sesamin, episesamin or mixtures thereof are preferably used. In addition, the metabolites of sesamin-class compounds (such as those described in JP 2001-139579 A) may be used in the present invention as the sesamin analogs included in the category of sesamin-class compounds of the present invention on the condition that they exhibit the effects of the present invention.

The sesamin-class compounds to be used in the present invention are not limited in any way by their form, production methods, and the like. If, for example, sesamin is chosen as the sesamin-class compound, sesame oil may be subjected to extraction by a known method (such as the one described in JP H04-9331 A) to obtain sesamin (hereinafter called a sesamin extract or concentrate), which is then used. Since the characteristic flavor of sesame oil is sometimes evaluated to be undesirable from an organoleptic viewpoint, the sesamin extract (or sesamin concentrate) may be rendered tasteless and odorless by a known means such as treatment with activated clay.

Thus, the sesamin-class compounds that are preferably used are the concentrates of sesamin-class compounds that are enriched in the concentration of sesamin-class compounds by extraction and/or purification from ingredients originating from foods such as sesame oil. The content may be set as appropriate for the kind of sesamin-class compounds to be used or the form of the composition in which the sesamin-class compounds are incorporated; the total content of sesamin-class compounds in their concentrates is generally at least 20 wt %, preferably at least 50 wt %, more preferably at least 70 wt %, and most preferably at least 90 wt %.

(Vitamin $B_1$ Class Compounds)

Vitamin $B_1$ class compounds are water-soluble vitamins also called thiamin and they are known to be converted to thiamine pyrophosphate (TPP) in vivo to participate in carbohydrate metabolism as a coenzyme for pyruvate dehydrogenase or to work as a coenzyme for α-ketoglutarate dehydrogenase in the TCA cycle.

The vitamin $B_1$ class compound of the present invention is the collective term for a series of compounds including thiamin and thiamin derivatives. Thiamin derivatives may be ones of disulfide form, acyl form, or mixtures thereof. Examples of thiamin derivatives include bistiamin, thiamine disulfide, thiamine dicetyl sulfate ester salts, benfotiamin, prosultiamin, fursultiamin, bisbentiamin, cycotiamin, octotiamin, aritiamin, thiamine propyl disulfide, thiamine tetrahydrofurfuryl disulfide, dicetiamin, bisbutythiamin, bisibutiamin, thiamine monophosphate disulfide, thiamine pyrophosphate, thiamine ethyl disulfide, thiamine propyl disulfide, etc. Among these, thiamin, thiamine disulfide, benfotiamin, fursultiamin, bisbentiamin, dicetiamin, thiamine ethyl disulfide, thiamine propyl disulfide, and mixtures thereof are preferably used as the vitamin $B_1$ class compounds of the present invention in view of their high stability. Furthermore, in addition to stability, benfotiamin, bisbentiamin, fursultiamin, thiamin or mixtures thereof are preferably used from the viewpoint of absorbability.

The vitamin $B_1$ compounds to be used in the present invention may in the form of medicinally, pharmaceutically, or physiologically acceptable salts. These salts may be exemplified by inorganic acid salts (e.g. hydrochlorides, sulfates, nitrates, hydrobromic acid salts, and phosphates), preferably hydrochlorides, sulfates, and nitrates, with hydrochlorides and nitrates being particularly preferred; specific examples include thiamine hydrochloride, thiamine nitrate, bistiamin nitrate, dicetiamin hydrochloride, fursultiamin hydrochloride, etc.

In the present invention, vitamin $B_1$ class compounds may be used either alone or in mixture of two or more species.

In the experiments conducted by the present inventors using fatigue animal models, which will be explained below in detail, no anti-fatigue action was observed in animal models when they were administered with a vitamin $B_1$ class compound independently (without being combined with sesamin-class compounds) at doses of 5 mg/kg, 10 mg/kg, 25 mg/kg, and 50 mg/kg {in terms of the amount of vitamin $B_1$ (mg) as calculated for thiamin per kg of the body weight of an animal model}. The anti-fatigue action was found enhanced when the vitamin $B_1$ class compound was administered in 100 mg/kg (see FIGS. 3 and 4).

(Compositions Incorporating at Least One Sesamin-Class Compound and at Least One Vitamin $B_1$ Class Compound)

The compositions of the present invention, on account of their incorporating sesamin-class compounds and vitamin $B_1$ class compounds, can provide synergistic enhancement of the anti-fatigue action which is one of the physiological activating effect of sesamin-class compounds. The compositions of the present invention can also be utilized as foods and beverages having high anti-fatigue action.

The total proportion of sesamin-class compounds as incorporated in the compositions of the present invention (e.g., pharmaceutical compositions, foods or beverages, and the like) is typically at least 1 wt %, preferably from 1 to 50 wt %, and more preferably from 1 to 10 wt %. The total proportion of vitamin $B_1$ class compounds as incorporated in the compositions is not limited in any particular way as long as it is within the range over which their effectiveness in synergistically enhancing the above-described anti-fatigue action of sesamin-class compounds is exhibited and it may be chosen as appropriate for such conditions as the form of the compositions and the pathological condition to be treated; vitamin $B_1$ class compounds are typically incorporated in 0.001 to 20 wt %, preferably in 0.01 to 10 wt %, and more preferably in 0.1 to 5 wt %, relative to the total quantity of the composition. Note that the amounts of vitamin $B_1$ class compounds are indicated herein in terms of the values as calculated for thiamin.

It is generally preferred that sesamin class compounds are ingested by adults in a daily dose of 1 to 200 mg, more preferably about 5 to 100 mg. The Ministry of Health, Labour and Welfare recommends that Japanese adults ingest at least 1.0 mg of vitamin $B_1$ class compounds a day. No upper limit is set for the daily intake of vitamin $B_1$ class compounds.

Depending on their total weight, the compositions of the present invention can incorporate sesamin-class compounds typically in amounts of 1 to 100 mg, preferably 1 to 60 mg, more preferably about 3 to 60 mg, and most preferably about 5 to 60 mg. The compositions can also incorporate vitamin $B_1$ class compounds typically in amounts of 1 to 100 mg, preferably about 5 to 50 mg. Generally speaking, incorporating more than 100 mg of vitamin $B_1$ class compounds is economically disadvantageous since their effectiveness in synergistically enhancing the anti-fatigue action is no longer expected and, what is more, depending on the kind of vitamin the $B_1$ class compound incorporated, its characteristic bitter taste and the like are considered to cause occasional drop in palatability.

It is preferred that the daily intakes of sesamin-class compounds and vitamin $B_1$ class compounds are adjusted to lie within the above ranges by administering the composition of the present invention at a frequency of one to three times per day.

(Beverages Containing at Least One Sesamin-Class Compound and at Least One Vitamin $B_1$ Class Compound)

By containing at least one sesamin-class compound and at least one vitamin $B_1$ class compound, there can be provided beverages with synergistic enhancement of the anti-fatigue action which is one of the physiological activating effects of sesamin-class compounds. The total content of sesamin-class compounds in the beverages of the present invention is typically from 1 to 100 mg, preferably from 1 to 60 mg, and more preferably from 1 to 20 mg, per 100 mL of the beverage. The total content of vitamin $B_1$ class compounds in the beverages is not limited in any particular way as long as it is within the range over which their effectiveness in synergistically enhancing the anti-fatigue action of sesamin-class compounds is exhibited and it typically ranges from about 1 to 100 mg, preferably from about 1 to 60 mg, and more preferably from about 1 to 20 mg, per 100 mL of the beverage.

Besides the sesamin-class compounds and vitamin $B_1$ class compounds, additives and other nutritional ingredients that are commonly used in beverages may appropriately be incorporated in the beverages of the present invention. Examples of such additives include antioxidants, sweeteners, acidulants, stabilizers, emulsifiers, flavoring agents, coloring agents, and preservatives. The beverages of the present invention may typically be served as packed in containers. Such containers are in ordinary forms and may be the same as those commonly used to pack beverages; they include, for example, containers molded from polyethylene terephthalate as the main component (PET bottles), metal cans, paper containers made from composites with metal foil or plastic film, and bottles.

In the experiments conducted by the present inventors using fatigue animal models, which will be explained below in detail, administering 10 mg/kg of sesamin-class compounds {in terms of the amount of sesamin-class compounds (mg) per kg of the body weight of an animal model} together with 5 to 10 mg/kg of a vitamins $B_1$ class compound caused a marked enhancement of the anti-fatigue action over the case where only two sesamin-class compounds were administered in 10 mg/kg (without administering a vitamin $B_1$ class compound) (see FIG. 2). As already mentioned, no anti-fatigue action was observed when only a vitamin $B_1$ class compound was orally administered in 5 to 10 mg/kg (see FIG. 3) but, surprisingly enough, the anti-fatigue action of sesamin-class compounds was markedly enhanced by adding equal amounts of a vitamin $B_1$ class compound.

In addition to the sesamin-class compounds and vitamin $B_1$ class compounds, the compositions of the present invention may incorporate any optional ingredients to an extent that will not impair the effects of the compositions. For example, physiologically active ingredients such as vitamins (e.g., vitamin E and vitamin C), minerals, hormones, nutritional ingredients and flavoring agents, as well as additives that are commonly incorporated in the pharmaceutical formulation procedure, such as emulsifiers, tonicity agents (isotonization agents), buffers, solvent promoters, antiseptics, stabilizers and antioxidants, may be incorporated as appropriate.

Since the compositions of the present invention provide an anti-fatigue action as enhanced synergistically by incorporating sesamin-class compounds and vitamin $B_1$ class compounds, they can also be utilized as health foods with advantage. Examples of health foods as referred to hereinafter include preparations or foods, such as capsules and tablets, in which the composition of the present invention itself that incorporates sesamin-class compounds and vitamin $B_1$ class compounds is contained as the active ingredient, as well as physiologically functional foods (foods for specified health use or FOSHU, and qualified FOSHU) that incorporate the composition as one ingredient so that they are provided with the anti-fatigue action and various other functions favorable to the living body. Also included in the category of the composition of the present invention are foods that are characterized by having the anti-fatigue action and which have a label attached thereto indicating that they relieve the fatigue in the living body or promote recovery from the fatigue.

The form of the health foods that contain sesamin-class compounds and vitamin $B_1$ class compounds is not limited in any particular way and they may be formulated in any desirable forms including, for example, solid forms such as powdery, granular or tablet forms, liquid forms such as solution, emulsion or dispersion forms, and semisolid forms such as a paste form.

The compositions of the present invention can also be utilized as pharmaceutical compositions. In this case, the compositions of the present invention may be formulated in dosage forms such as liquids, tablets, granules, powders, capsules, dry syrups or pills, and administered perorally; alternatively, they may be formulated as an injection for parenteral administration. The mode of administration can be chosen as appropriate for the pathological condition, its progress, and other conditions.

(Anti-Fatigue Action and Anti-Fatigue Agents)

The compositions of the present invention are also useful as anti-fatigue agents in humans and non-human animals. The term "non-human animals" as used herein refers to industrial animals, pets, and laboratory animals; specifically, the term "industrial animals" refers to farm animals such as cattle, horse, swine, goat, sheep, etc., as well as racehorses, hunting dogs, etc.; the term "pets" refers to dog, cat, marmoset, hamster, etc.; the term "laboratory animals" refers to mouse, rat, guinea pig, beagle, miniature pig, rhesus monkey, crab-eating monkey, and other animals that are subjected to research in such fields as medicine, biology, agronomy, pharmacy, etc. The anti-fatigue agents of the present invention are used in humans, industrial animals, pets and laboratory animals that perceive fatigue, and they are used with particular advantage in humans.

Fatigue as appears here is a temporary lowering of physical or mental performance that results from continued application of a physical or mental stress and lowered performance means a drop in the quality or quantity of a physical or mental working capacity. It should also be noted that the term "fatigue" as used herein covers chronic fatigue syndrome and death by overwork.

The anti-fatigue agents of the present invention are those agents which have an action for attenuating the above-defined fatigue or achieving recovery from it, as specifically described by the following effects: prolonging the duration for which a moving or acting site (including the brain) keeps functioning, and controlling the increase in fatigue-causing substances given the same amount of motion or action (improvement of stamina and increase of body strength); or ameliorating such a condition that the brain or nerves have come to perceive fatigue although a moving or acting site is yet to get tired, and promoting the recovery of the moving or acting site from the tired state to the normal state.

Chronic fatigue syndrome which is to be treated with the anti-fatigue agents of the present invention means general symptoms such as systemic feelings of weariness (tiredness) and malaise (lassitude), slight fever, lymph node dilation, muscle pain, joint pain, and psychoneurotic symptoms, all being so prolonged as to potentially interfere with the daily life of the affected individual. The anti-fatigue agents of the present invention are capable of treating chronic fatigue syndrome; in other words, they can palliate the various symptoms of chronic fatigue syndrome such that the affected individual is brought to the normal condition. Death by overwork which is also to be treated with the anti-fatigue agents of the present invention means such a condition of individuals who are under too extreme fatigue to be capable of keeping physical vigor and yet they cannot fully perceive fatigue, with the result that cardiovascular disease or cardiac disease manifests itself, causing the individuals to become permanently unable to work or bringing them to death. The anti-fatigue agents of the present invention are capable of treating chronic fatigue syndrome, whereby they can prevent death from overwork. The anti-fatigue action in the present invention, or its effectiveness as "anti-fatigue agents" can be verified by such a method as measuring the swimming time in a water immersion sleep deprivation test. Mice that have been kept in an environment such as water immersion where they are unable to have a good sleep or take a rest position so they cannot have a physical or mental rest are forced to swim under a weight load and the critical swimming time (e.g., the time it takes for the mouse to have its nose first submerged in the water for a period of ten seconds or longer or the time it takes for the mouse to have its nose finally submerged in the water (and incapable of rising up to its surface again)) is measured to confirm the degree of their fatigue. Since this is an animal model for physical or mental fatigue, an extension of the swimming time as achieved by administering it with the test substance means the verification of resistance to fatigue, as exemplified by prevention or relief of physical and/or mental fatigue or any accompanying muscle or other pains, a sufficient increase in body strength to extend the time to total exhaustion, and maintenance of physical vigor in the tired model.

The anti-fatigue agents of the present invention have the advantage that one who ingests them will not easily get tired and they are also effective in achieving recovery from fatigue. To be more specific, if one feels a physical fatigue after having a muscular exercise as in sports or feels a mental fatigue after performing a continuous task such as calculation, they may ingest the anti-fatigue agent of the present invention to recover from the fatigue; if they ingest the anti-fatigue agent before working or sporting, they can be prevented from getting tired. If the anti-fatigue agent is ingested before or during sporting, it is expected to improve stamina. As a further advantage, mental fatigue as well as diseases that accompany it can also be prevented by ingesting the anti-fatigue agent on a regular basis.

The anti-fatigue agents of the present invention may be administered perorally in various forms including liquids, tablets, granules, powders, capsules, dry syrups, pills and the like; they may also be administered parenterally in such a form as injection; the mode of administration can be chosen as appropriate for the pathological condition, its progress, and other conditions. Since sesamin-class compounds as an active ingredient in the present invention are fat-soluble whereas vitamin $B_1$ class compounds as the other active ingredient are water-soluble, the two classes of compounds may be ingested in different forms. To be more specific, two preparations, one containing the sesamin-class compounds and the other containing the vitamin $B_1$ class compounds, are formulated separately and then administered almost simultaneously or, alternatively, one preparation is first administered and while its effect persists, the other preparation is administered; in this way, an enhancement of the anti-fatigue action of sesamin-class compounds as intended by the present invention can be achieved. Hence, a kit comprising two preparations, one containing sesamin-class compounds and the other containing vitamin $B_1$ class compounds, is also included in the scope of the anti-fatigue agents of the present invention.

The present invention is described in greater detail by means of the following examples, to which the present invention is in no way limited.

Example 1

Anti-Fatigue Action (1) from Vitamin $B_1$ Class Compound and Sesamin-Class Compounds A sesamin/episesamin mixture (sesamin:episesamin=5:5 in weight ratio) was used as sesamin-class compounds under test and thiamine hydrochloride (from NACALAI TESQUE) was used as a vitamin $B_1$ class compound.

The anti-fatigue effect was evaluated by the following partial modification of the method of Tanaka et al. (Neuroscience, Let. 352, 159-162, 2003): Balb/c male mice (8-week old) were purchased from Japan SLC, Inc. and conditioned in a test environment for a week, and the animals that had grown normally were subjected to the test. They were divided into five groups, as identified in Table 1, such that each group consisted of 10 animals and had the same average body weight. The values indicated in Table 1 for the amount of vitamin $B_1$ class compound administered are based on the amount of thiamine hydrochloride as calculated for thiamin. Four of those five groups were water immersion groups under stress from sleep deprivation, which were kept in breeding cages, not on paper chips but in tap water (23° C.) supplied to a depth of 7 mm, thereby depriving the mice of sleep. During a two-day immersion in water to deprive sleep, the mice were administered orally with the associated test samples for two days on a one-dose-a-day basis. Of the two test samples, the sesamin-class compounds were dissolved in olive oil and the thiamin in distilled water. The order of administration was the thiamin followed by the sesamin-class compounds; as controls, distilled water and olive oil were administered orally.

After two days of keeping under immersion in water or normal keeping, each mouse was fitted with a weight at the tail which corresponded to 8% of its body weight, and was allowed to swim in a water tank of 18 cm$^\phi$ that was filled with water to a depth of 30 cm; the time it took for each mouse to have its nose first submerged in the water for a period of at least 10 seconds was measured as the critical swimming time. The critical swimming time of the mice in the groups kept under immersion in water (under stress from deprivation of sleep under immersion in water) was shorter than that of the mice in the normally kept group. The degree by which the administration of the test samples (sesamin-class compounds and/or vitamin $B_1$ class compound) could shorten the critical swimming time was measured to evaluate the anti-fatigue action of the test samples.

TABLE 1

| Group | Method of breeding | Test Samples | |
|---|---|---|---|
| | | Amount of sesamin-class compounds administered(mg/kg*) | Amount of Vitamin $B_1$ class compound administered(mg/kg*) |
| Control group | Normal | 0 (olive oil administered) | 0 (distilled water administered) |
| Comparative group 1 | Immersion in water | 0 (olive oil administered) | 0 (distilled water administered) |
| Comparative group 2 | Immersion in water | 0 (olive oil administered) | 50 |
| Comparative group 3 | Immersion in water | 50 | 0 (distilled water administered) |
| Test group 1 | Immersion in water | 50 | 50 |

*the amount (mg) administered per kg of mouse's body weight

The results are shown in FIG. 1, from which it is clear that the critical swimming time of the mice in comparative group 1 that were kept under immersion in water was shorter than that of the mice in the normally kept group (control group). The group administered with 50 mg/kg of vitamin $B_1$ class compound as the test sample (comparative group 2) had no recognizable change in critical swimming time from comparative group 1. The group administered with 50 mg/kg of sesamin-class compounds (comparative group 3) had a somewhat longer critical swimming time than comparative group 1. The group administered with each of vitamin $B_1$ class compound and sesamin-class compounds in the amount of 50 mg/kg (test group 1) had a markedly longer critical swimming time than comparative group 1. These results show that the anti-fatigue action was synergistically enhanced by combined administration of vitamin $B_1$ class compound and sesamin-class compounds.

Example 2

Anti-Fatigue Action (2) from Vitamin $B_1$ Class Compound and Sesamin-Class Compounds The anti-fatigue action from vitamin $B_1$ class compound and sesamin-class compounds was evaluated as in Example 1, except that the mice were divided into six groups as identified in Table 2 and that the time it took for each mouse to have its nose finally submerged in water (and incapable of rising up to its surface again) was measured as the critical swimming time. The values indicated in Table 2 for the amount of vitamin $B_1$ class compound administered are based on the amount of thiamine hydrochloride as calculated for thiamin.

TABLE 2

| Group | Method of breeding | Amount of sesamin-class compounds administered(mg/kg*) | Amount of Vitamin $B_1$ class compound administered(mg/kg*) |
|---|---|---|---|
| Control group | Normal | 0 (olive oil administered) | 0 (distilled water administered) |
| Comparative group 4 | Immersion in water | 0 (olive oil administered) | 0 (distilled water administered) |
| Comparative group 5 | Immersion in water | 0 (olive oil administered) | 10 |
| Comparative group 6 | Immersion in water | 10 | 0 (distilled water administered) |
| Test group 2 | Immersion in water | 10 | 5 |
| Test group 3 | Immersion in water | 10 | 10 |

*the amount (mg) administered per kg of mouse's body weight

Figure 2:
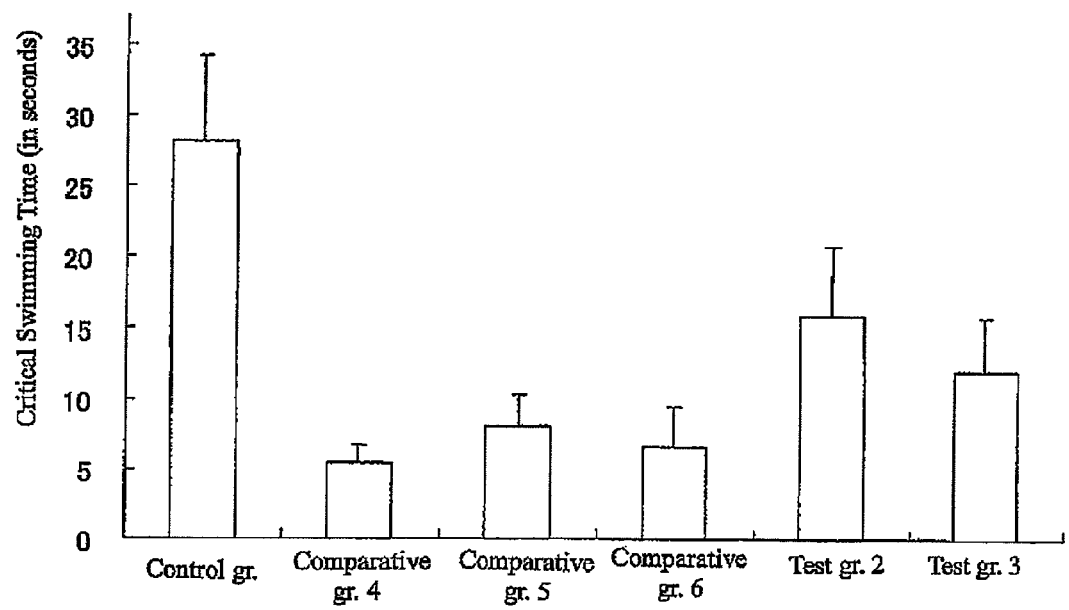
FIG. 2 shows critical swimming times for a normally kept group (control group), a group kept immersed in water (comparative group 4), a group of mice kept immersed in water under administration with 10 mg/kg of a vitamin $B_1$ class compound (comparative group 5), a group of mice kept immersed in water under administration with 10 mg/kg of sesamin-class compounds (comparative group 6), a group of mice kept immersed in water under administration with 5 mg/kg of the vitamin $B_1$ class compound and 10 mg/kg of the sesamin-class compounds (test group 2), and a group of mice kept immersed in water under administration with 10 mg/kg of the vitamin $B_1$ class compound and 10 mg/kg of the sesamin-class compounds (test group 3)

The results are shown in FIG. 2, from which it is clear that the critical swimming time of the mice in comparative group 4 that were kept under immersion in water was shorter than that of the mice in the normally kept group (control group). The groups administered with 5 mg/kg or 10 mg/kg of vitamin $B_1$ class compound together with 10 mg/kg of sesamin-class compound (test groups 2 and 3) had markedly longer critical swimming times than comparative group 4. These results show that the anti-fatigue action was synergistically enhanced by combined administration of vitamin $B_1$ class compound and sesamin-class compounds.

Example 3

Reference Example

Anti-Fatigue Action from Independent Administration of Vitamin $B_1$ Class Compound The anti-fatigue action from independent administration of vitamin $B_1$ class compound was evaluated as in Example 1, except that the mice were divided into nine groups as identified in Tables 3 and 4. The values indicated in Tables 3 and 4 for the amount of vitamin $B_1$ class compound administered are based on the amount of thiamine hydrochloride as calculated for thiamin.

Figure 3:
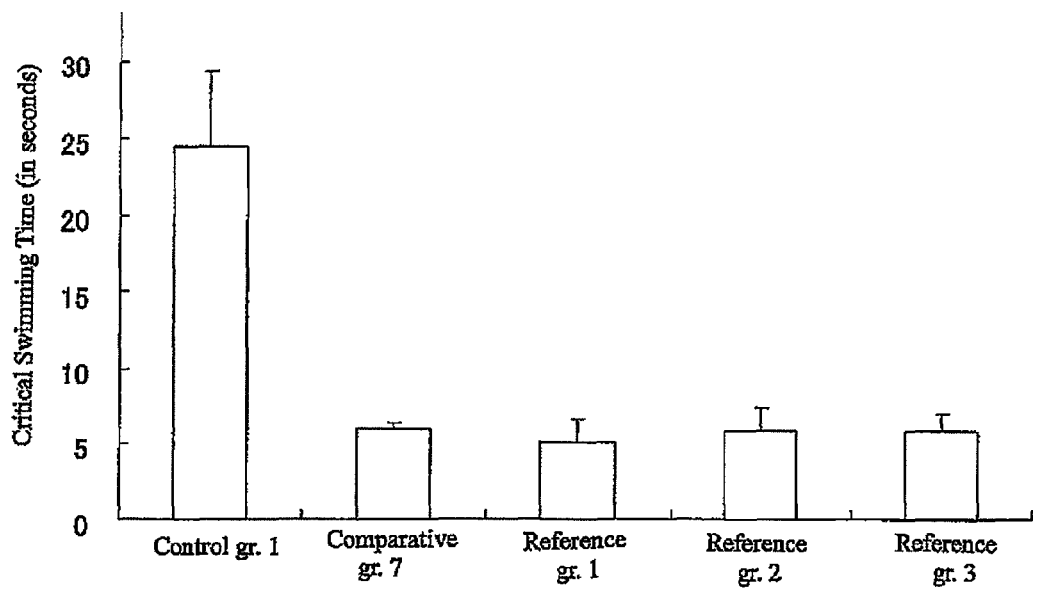
FIG. 3 shows critical swimming times for a normally kept group (control group 1), a group kept immersed in water (comparative group 7), and groups of mice kept immersed in water under administration with 5 mg/kg, 10 mg/kg, and 25 mg/kg of the vitamin $B_1$ class compound (reference groups 1 to 3, respectively)
Figure 4:
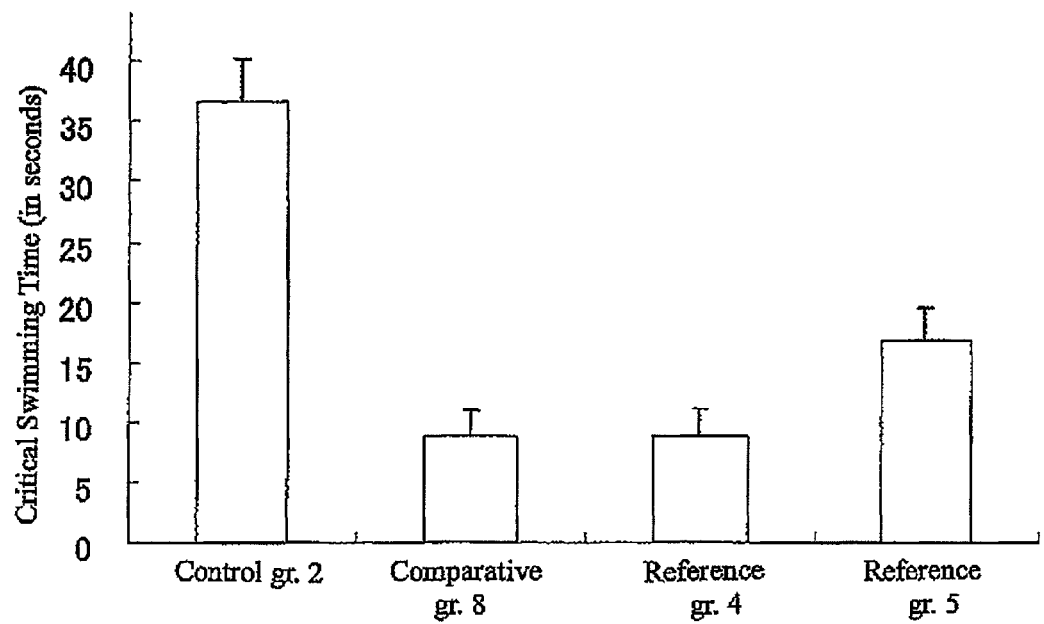
FIG. 4 shows critical swimming times for a normally kept group (control group 2), a group kept immersed in water (comparative group 8), and groups of mice kept immersed in water under administration with 50 mg/kg and 100 mg/kg of the vitamin $B_1$ class compound (reference groups 4 and 5, respectively).

The results are shown in FIGS. 3 and 4, from which it is clear that the critical swimming time of the mice in comparative groups 7 and 8 that were kept under immersion in water were shorter than those of the mice in the normally kept groups (control groups 1 and 2). The groups administered with 5 mg/kg, 10 mg/kg, 25 mg/kg or 50 mg/kg of vitamin $B_1$ class compound (reference groups 1 to 4) had comparable critical swimming times to comparative groups 7 and 8. The group administered with 100 mg/kg of vitamin $B_1$ class compound (reference group 5) had a longer critical swimming time than comparative group 8.

Example 4

Preparation 1: Granules

| Sesamin | 10 g |
|---|---|
| Thiamine hydrochloride | 10 g |
| Tocopherol acetate | 50 g |
| Silicic anhydride | 20 g |
| Corn starch | 110 g |

TABLE 3

| Group | Method of breeding | Amount of sesamin-class compounds administered(mg/kg*) | Amount of Vitamin $B_1$ class compound administered(mg/kg*) |
|---|---|---|---|
| Control group 1 | Normal | 0 (olive oil administered) | 0 (distilled water administered) |
| Comparative group 7 | Immersion in water | 0 (olive oil administered) | 0 (distilled water administered) |
| Reference group 1 | Immersion in water | 0 (olive oil administered) | 5 |
| Reference group 2 | Immersion in water | 0 (olive oil administered) | 10 |
| Reference group 3 | Immersion in water | 0 (olive oil administered) | 25 |

*the amount (mg) administered per kg of mouse's body weight

TABLE 4

| Group | Method of breeding | Amount of sesamin class compounds administered(mg/kg*) | Amount of Vitamin $B_1$ class compound administered(mg/kg*) |
|---|---|---|---|
| Control group 2 | Normal | 0 (olive oil administered) | 0 (distilled water administered) |
| Comparative group 8 | Immersion in water | 0 (olive oil administered) | 0 (distilled water administered) |
| Reference group 4 | Immersion in water | 0 (olive oil administered) | 50 |
| Reference group 5 | Immersion in water | 0 (olive oil administered) | 100 |

*the amount (mg) administered per kg of mouse's body weight

The powders of these ingredients were mixed uniformly; after adding 100 mL of 10% hydroxypropyl cellulose in ethanol, the mixture was kneaded in the usual manner, extruded and dried to prepare granules.

Preparation 2: Capsules

|  |  |
|---|---|
| Gelatin | 60.0% |
| Glycerin | 30.0% |
| Methyl paraoxybenzoate | 0.15% |
| Propyl paraoxybenzoate | 0.51% |
| Water | q.s. |

A composition comprising the ingredients indicated below was filled into gelatin shells consisting of the above-mentioned ingredients by a conventional method to prepare soft capsules each weighing 360 mg.

|  |  |
|---|---|
| Sesamin | 3.5 mg |
| Thiamine hydrochloride | 0.4 mg |
| Fatty acid ester of glycerol | 15.0 mg |
| Beeswax | 15.0 mg |
| Wheat germ oil | 245 mg |

Preparation 3: Tablets

|  |  |
|---|---|
| Sesamin | 10 g |
| Thiamine nitrate | 30 g |
| Starch | 172 g |
| Fatty acid of sucrose | 9.0 g |
| Silicon oxide | 9.0 g |

These ingredients were mixed and palletized with a single-action tableting machine to prepare 9-mm$^\phi$ tablets each weighing 300 mg.

Preparation 4: Beverage

|  |  |
|---|---|
| Palatability: Sodium DL-tartrate | 0.1 g |
| Succinic acid | 0.009 g |
| Sweetness: Liquid sugar | 800 g |
| Acidity: Citric acid | 12 g |
| Vitamin C | 10 g |
| Sesamin | 1 g |
| Vitamin $B_1$ | 1 g |
| Vitamin E | 20 g |
| Cyclodextrin | 5 g |
| Emulsifier | 5 g |
| Flavoring agent | 15 mL |
| Potassium chloride | 1 g |
| Magnesium sulfate | 0.5 g |

These ingredients were mixed together and diluted with water to make a total of 10 L. The resulting beverage was intended to be drunk in a volume of about 100 mL per serving.

The invention claimed is:

1. A composition comprising at least one sesamin-class compound and at least one vitamin B1 class compound,
    wherein the total amount of the sesamin class compound is from 1 to 10 wt % of the total weight of the composition;
    wherein the total amount of the vitamin B1 class compound is from 0.1 to 5 wt %;
    wherein the sesamin-class compound is selected from the group consisting of episesamin, sesamin, sesaminol, episesaminol, sesamolin, and combinations thereof; and
    wherein the vitamin B1 class compound is selected from the group consisting of thiamin, thiamine disulfide, benfotiamin, fursultiamin, bisbentiamin, dicetiamin, thiamine ethyl disulfide, thiamine propyl disulfide, and salts and combinations thereof.

2. The composition according to claim 1, wherein the sesamin-class compound is sesamin, episesamin, or a mixture thereof.

3. The composition according to claim 1, which is for oral use.

4. The composition according to claim 1, which is a food or a beverage.

5. A method of treating a fatigue condition, which comprises administering a composition containing at least one sesamin-class compound and at least one vitamin of B1 class compound to a subject in need of treatment;
    wherein the total amount of the sesamin class compound is from 1 to 10 wt % of the composition;
    wherein the total amount of the vitamin B1 class compound is from 0.1 to 5 wt %;
    wherein the sesamin-class compound is selected from the group consisting of sesamin, episesamin, sesaminol, episesaminol, sesamolin and combinations thereof; and
    wherein the vitamin B1 class compound is selected from the group consisting of thiamin, thiamine disulfide, benfotiamin, fursultiamin, bisbentiamin, dicetiamin, thiamine ethyl disulfide, thiamine propyl disulfide, salts and combinations thereof.

6. The composition of claim 1, wherein the amount of sesamin class compounds and the amount of vitamin B1 class compounds is a ratio from 1:1 to 2:1.

7. The method of claim 5, wherein the amount of sesamin class compounds and the amount of vitamin B1 class compounds is a ratio from 1:1 to 2:1.

8. The composition of claim 1, wherein the sesamin-class compound is selected from the group consisting of episesamin, sesamin, and combinations thereof; and wherein the vitamin B1 class compound is selected from the group consisting of thiamin, thiamine disulfide, thiamine ethyl disulfide, thiamine propyl disulfide, and salts and combinations thereof.

* * * * *